United States Patent
Alferness et al.

(10) Patent No.: US 8,277,372 B2
(45) Date of Patent: Oct. 2, 2012

(54) CARDIAC SUPPORT DEVICE WITH DIFFERENTIAL COMPLIANCE

(75) Inventors: Clifton A. Alferness, Redmond, WA (US); Jai Shankar Raman, North Baldwyn (AU); John Melmouth Power, Williamstown (AU)

(73) Assignee: Mardil, Inc., Plymouth, MN (US)

( * ) Notice: Subject to any disclaimer, the term of this patent is extended or adjusted under 35 U.S.C. 154(b) by 0 days.

(21) Appl. No.: 12/719,553

(22) Filed: Mar. 8, 2010

(65) Prior Publication Data

US 2010/0160721 A1    Jun. 24, 2010

Related U.S. Application Data

(63) Continuation of application No. 11/469,224, filed on Aug. 31, 2006, now abandoned, which is a continuation of application No. 10/809,962, filed on Mar. 26, 2004, now Pat. No. 7,578,784, which is a continuation of application No. 09/880,576, filed on Jun. 13, 2001, now abandoned, which is a continuation of application No. 09/565,621, filed on May 4, 2000, now Pat. No. 6,537,203, which is a continuation of application No. 09/114,510, filed on Jul. 13, 1998, now Pat. No. 6,123,662.

(51) Int. Cl.
*A61F 2/02*    (2006.01)
(52) U.S. Cl. .......................................... 600/37
(58) Field of Classification Search .................... 600/37, 600/16–18; 128/897, 898
See application file for complete search history.

(56) References Cited

U.S. PATENT DOCUMENTS 3,811,411 A * 5/1974 Moeller .................... 119/241
5,558,617 A * 9/1996 Heilman et al. ............ 600/16

* cited by examiner

*Primary Examiner* — Samuel Gilbert
(74) *Attorney, Agent, or Firm* — Gordon & Rees LLP; Laurie A. Axford; David Heckadon

(57) ABSTRACT

A cardiac support device comprising a jacket of flexible and biocompatible material having a first axis for alignment generally parallel to a longitudinal axis of a patient's heart and a second axis that is transverse to the first axis. The material exhibits an amount of expansion in response to a force applied to the material along the first axis that is different than an amount of expansion in response to the force applied to the material along the second axis.

14 Claims, 7 Drawing Sheets

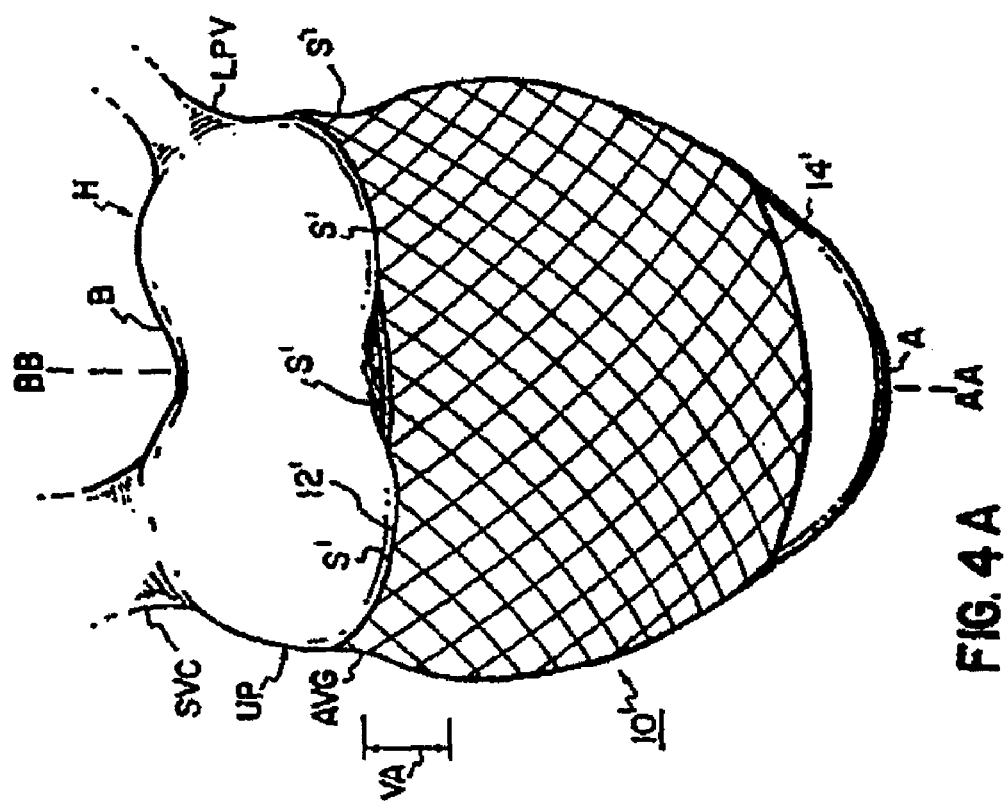
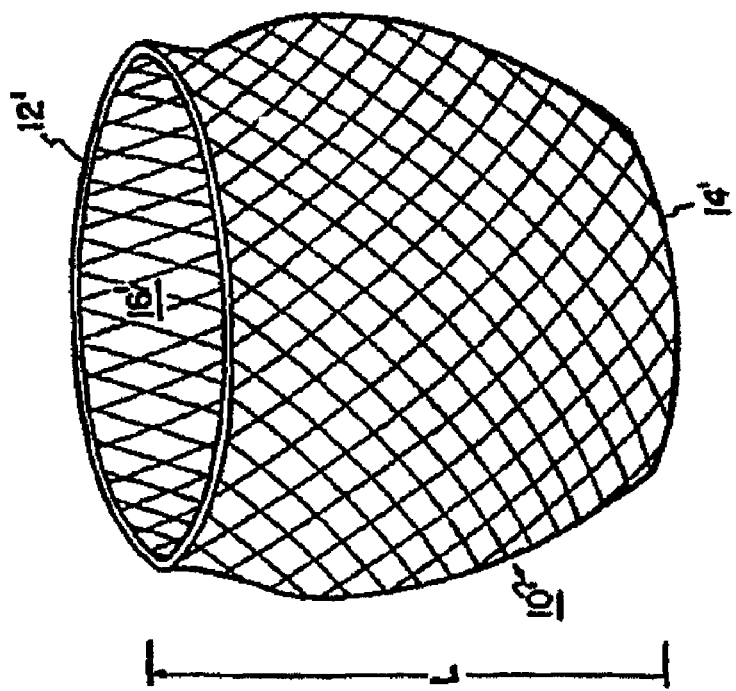

CARDIAC SUPPORT DEVICE WITH DIFFERENTIAL COMPLIANCE

REFERENCE TO RELATED APPLICATIONS

This application is a continuation of application Ser. No. 11/469,224, filed Aug. 31, 2006, pending, which is a continuation of application Ser. No. 10/809,962, filed Mar. 26, 2004, now U.S. Pat. No. 7,578,784, which is a continuation of application Ser. No. 09/880,576, filed Jun. 13, 2001, now abandoned, which is a continuation of application Ser. No. 09/565,621, filed May 4, 2000, now U.S. Pat. No. 6,537,203, which is a continuation of application Ser. No. 09/114,510, filed Jul. 13, 1998, now U.S. Pat. No. 6,123,662, all of which are incorporated herein by reference in their entirety.

FIELD OF THE INVENTION

The present invention pertains to a device and method for treating heart disease. More particularly, the present invention is directed to a method and device for treating congestive heart disease and related valvular dysfunction.

DESCRIPTION OF THE PRIOR ART

Congestive heart disease is a progressive and debilitating illness. The disease is characterized by a progressive enlargement of the heart.

As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Patients suffering from congestive heart disease are commonly grouped into four classes (i.e., Classes I, II, III and IV). In the early stages (e.g., Classes I and II), drug therapy is the commonly proscribed treatment. Drug therapy treats the symptoms of the disease and may slow the progression of the disease. Importantly, there is no cure for congestive heart disease. Even with drug therapy, the disease will progress. Further, the drugs may have adverse side effects.

Presently, the only permanent treatment for congestive heart disease is heart transplant. To qualify, a patient must be in the later stage of the disease (e.g., Classes III and IV with Class IV patients given priority for transplant). Such patients are extremely sick individuals. Class III patients have marked physical activity limitations and Class IV patients are symptomatic even at rest.

Due to the absence of effective intermediate treatment between drug therapy and heart transplant, Class III and IV patients will have suffered terribly before qualifying for heart transplant. Further, after such suffering, the available treatment is unsatisfactory. Heart transplant procedures are very risky, extremely invasive and expensive and only shortly extend a patient's life. For example, prior to transplant, a Class IV patient may have a life expectancy of 6 months to one-year. Heart transplant may improve the expectancy to about five years.

Unfortunately, not enough hearts are available for transplant to meet the needs of congestive heart disease patients. In the United States, in excess of 35,000 transplant candidates compete for only about 2,000 transplants per year. A transplant waiting list is about 8-12 months long on average and frequently a patient may have to wait about 1-2 years for a donor heart. While the availability of donor hearts has historically increased, the rate of increase is slowing dramatically. Even if the risks and expense of heart transplant could be tolerated, this treatment option is becoming increasingly unavailable. Further, many patient's do not qualify for heart transplant for failure to meet any one of a number of qualifying criteria.

Congestive heart failure has an enormous societal impact. In the United States alone, about five million people suffer from the disease (Classes I through IV combined). Alarmingly, congestive heart failure is one of the most rapidly accelerating diseases (about 400,000 new patients in the United States each year). Economic costs of the disease have been estimated at $38 billion annually.

Not surprising, substantial effort has been made to find alternative treatments for congestive heart disease. Recently, a new surgical procedure has been developed. Referred to as the Batista procedure, the surgical technique includes dissecting and removing portions of the heart in order to reduce heart volume. This is a radical new and experimental procedure subject to substantial controversy. Furthermore, the procedure is highly invasive, risky and expensive and commonly includes other expensive procedures (such as a concurrent heart valve replacement). Also, the treatment is limited to Class IV patients and, accordingly, provides no hope to patients facing ineffective drug treatment prior to Class IV. Finally, if the procedure fails, emergency heart transplant is the only available option.

Clearly, there is a need for alternative treatments applicable to both early and later stages of the disease to either stop the progressive nature of the disease or more drastically slow the progressive nature of congestive heart disease. Unfortunately, currently developed options are experimental, costly and problematic.

Cardiomyoplasty is a recently developed treatment for earlier stage congestive heart disease (e.g., as early as Class III dilated cardiomyopathy). In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., Reverse Remodeling From Cardiomyoplasty In Human Heart Failure: External Constraint Versus Active Assist, 91 Circulation 2314-2318 (1995).

Even though cardiomyoplasty has demonstrated symptomatic improvement, studies suggest the procedure only minimally improves cardiac performance. The procedure is highly invasive requiring harvesting a patient's muscle and an open chest approach (i.e., sternotomy) to access the heart.

Furthermore, the procedure is expensive—especially those using a paced muscle. Such procedures require costly pacemakers. The cardiomyoplasty procedure is complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole.

In addition to cardiomyoplasty, mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle and into the aorta. An example of such is shown in U.S. Pat. No. 4,995,857 to Arnold dated Feb. 26, 1991. LVAD surgeries are still in U.S. clinical trials and not generally available. Such surgeries are expensive. The devices are at risk of mechanical failure and frequently require external power supplies. TAH devices, such as the celebrated Jarvik heart, are used as temporary measures while a patient awaits a donor heart for transplant.

Other attempts at cardiac assist devices are found in U.S. Pat. No. 4,957,477 to Lundbäck dated Sep. 18, 1990, U.S. Pat. No. 5,131,905 to Grooters dated Jul. 21, 1992 and U.S. Pat. No. 5,256,132 to Snyders dated Oct. 26, 1993. Both of the Grooters and Snyders patents teach cardiac assist devices which pump fluid into chambers opposing the heart to assist systolic contractions of the heart. The Lundbäck patent teaches a double-walled jacket surrounding the heart. A fluid fills a chamber between the walls of the jacket. The inner wall is positioned against the heart and is pliable to move with the heart. Movement of the heart during beating displaces fluid within the jacket chamber.

Commonly assigned U.S. Pat. No. 5,702,343 to Alferness dated Dec. 30, 1997 teaches a jacket to constrain cardiac expansion during diastole. The present invention pertains to improvements to the invention disclosed in the '343 patent.

SUMMARY OF THE INVENTION

On embodiment of the invention is an improved cardiac support device comprising a jacket of flexible and biocompatible material having first and second non-parallel axes. The material exhibits an amount of expansion in response to a force applied to the material along the first axis that is different than an amount of expansion in response to the force applied to the material along the second axis. In another embodiment the first and second axes are transverse to one another. The first axis can be generally parallel to a longitudinal axis of the patient's heart.

BRIEF DESCRIPTION OF THE DRAWINGS

FIG. 4 is a perspective view of a second embodiment of a cardiac constraint device according to the present invention;

FIG. 4A is a side elevation view of a diseased heart in diastole with the device of FIG. 4 in place;

DETAILED DESCRIPTION OF THE PREFERRED EMBODIMENTS

Figure 1A:
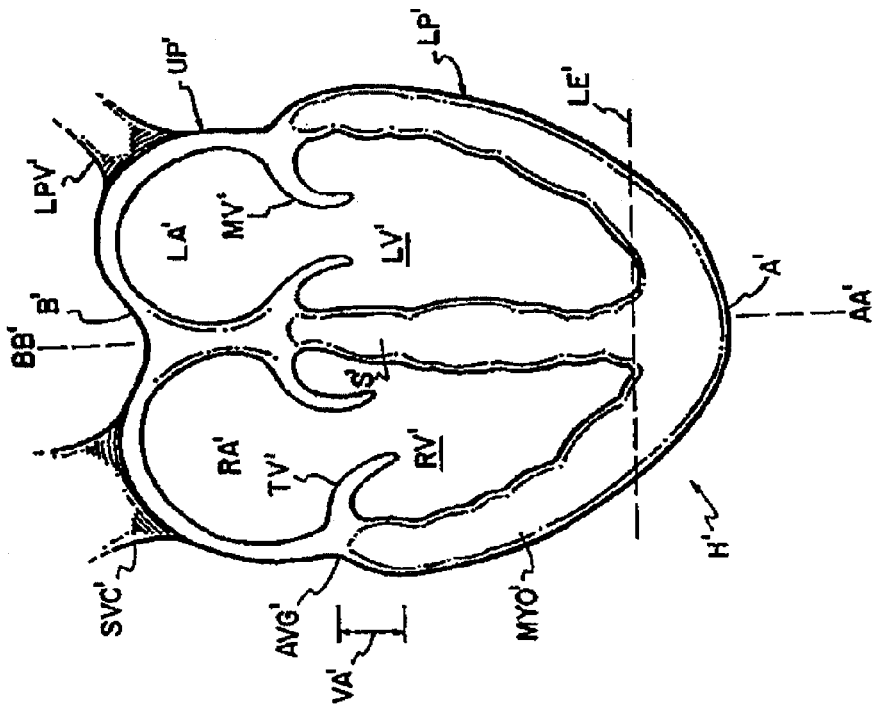
FIG. 1A is the view of FIG. 1 showing the heart during diastole.
Figure 1:
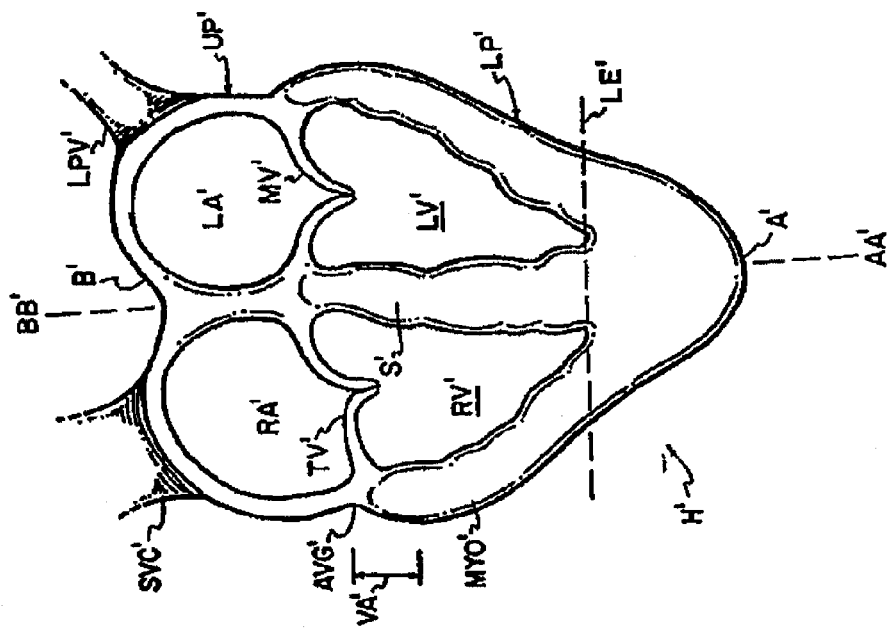
FIG. 1 is a schematic cross-sectional view of a normal, healthy human heart shown during systole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The heart H' has a length measured along a longitudinal axis AA'-BB' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V groove AVG'. Extending away from the upper portion UP' are a plurality of major blood vessels communicating with the chambers RA', RV', LA', LV'. For ease of illustration, only the superior vena cava SVC' and a left pulmonary vein LPV' are shown as being representative.

The heart H' contains valves to regulate blood flow between the chambers RA', RV', LA', LV' and between the chambers and the major vessels (e.g., the superior vena cava SVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'-BB').

The motion of the heart H' and the variation in the shape of the heart H' during contraction and expansion is complex. The amount of motion varies considerably throughout the heart H'. The motion includes a component which is parallel to the axis AA'-BB' (conveniently referred to as longitudinal expansion or contraction). The motion also includes a component perpendicular to the axis AA'-BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2B:
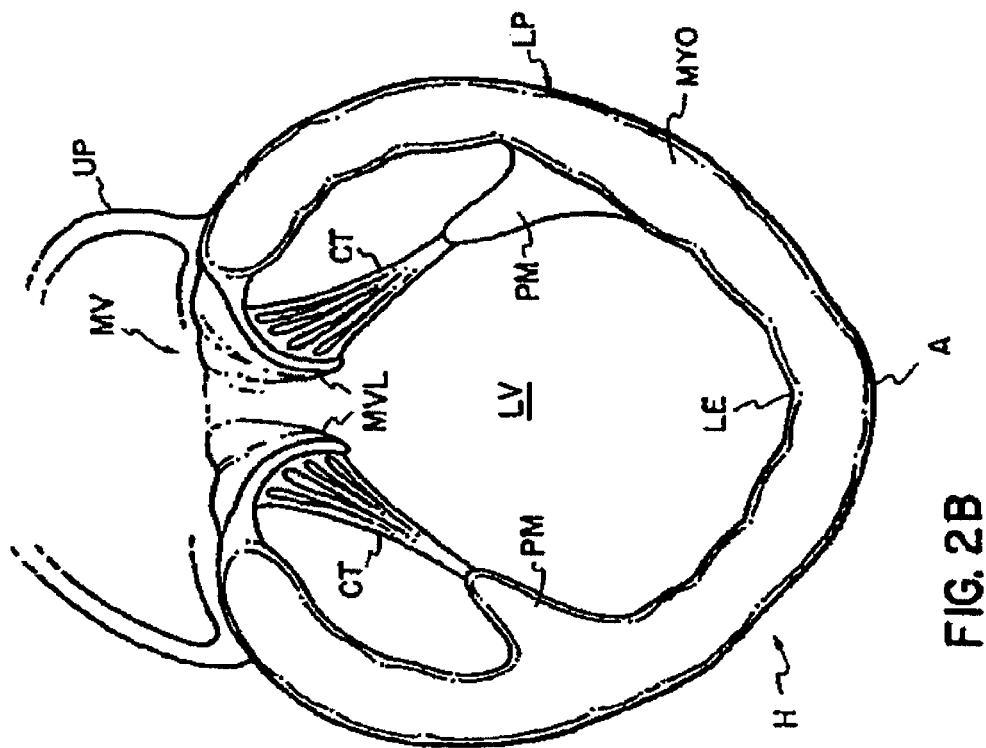
FIG. 2B is the view of FIG. 1B showing a diseased heart.
Figure 2A:
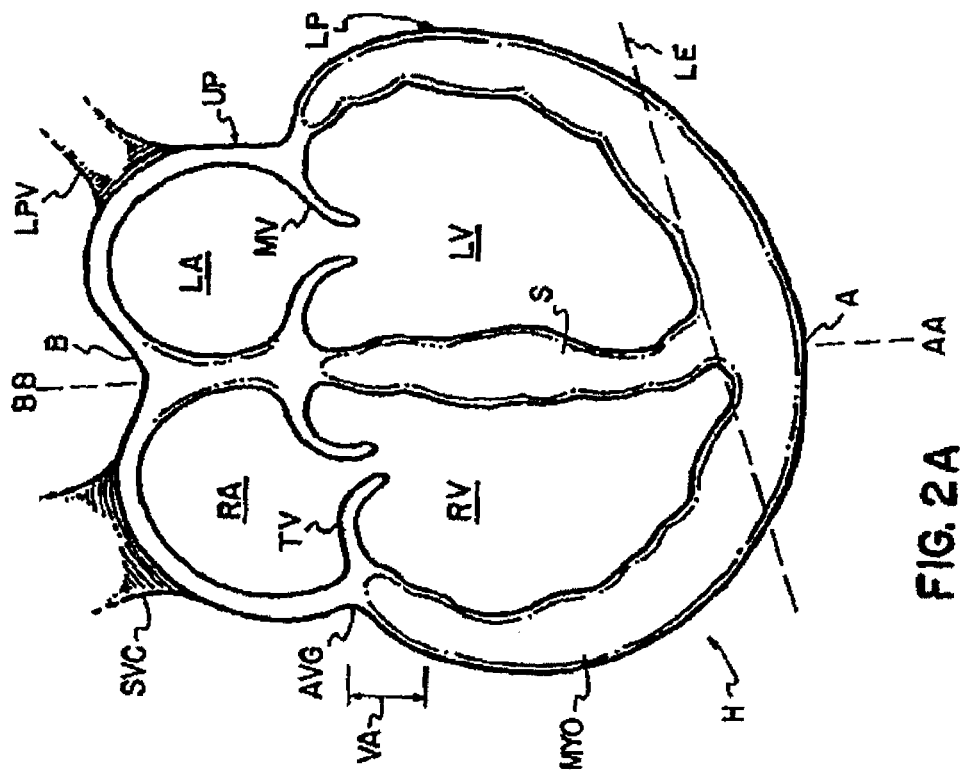
FIG. 2A is the view of FIG. 2 showing the heart during diastole.
Figure 2:
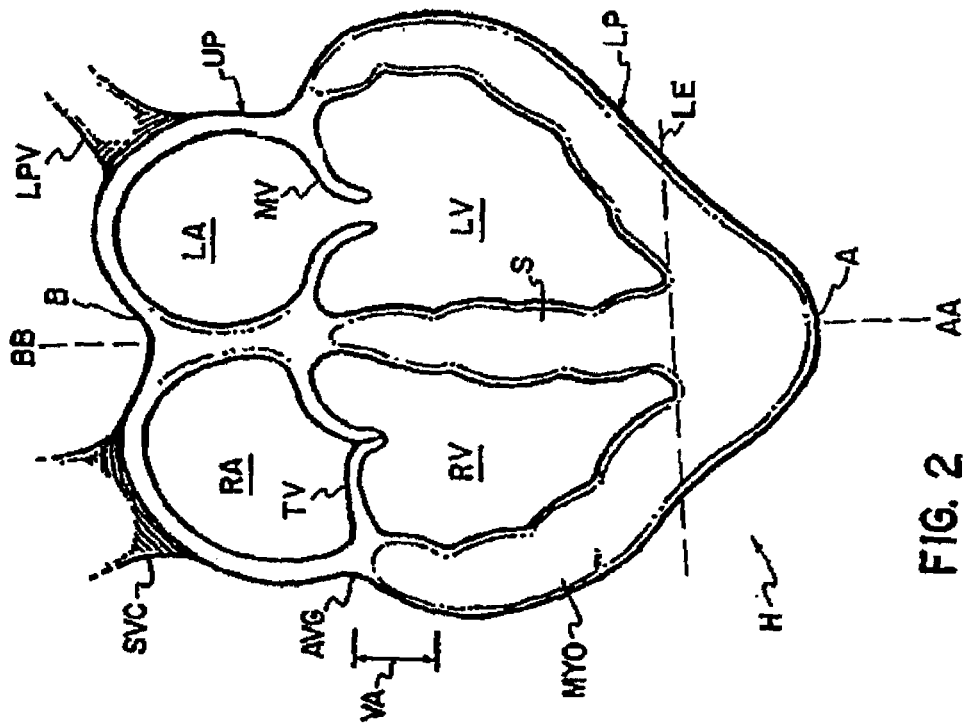
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H bulges outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic insufficiency.

For ease of illustration, the progression of congestive heart disease has been illustrated and described with reference to a progressive enlargement of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close (as illustrated by the mitral valve MV in FIG. 2A). Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H. This is best described with reference to FIGS. 1B and 2B.

Figure 1B:
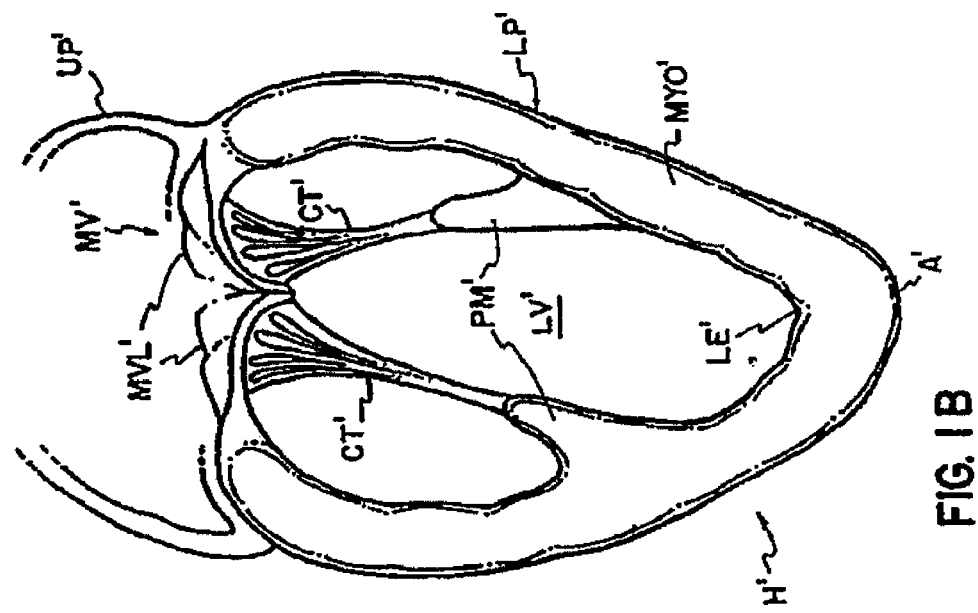
FIG. 1B is a view of a left ventricle of a healthy heart as viewed from a septum and showing a mitral valve.

FIGS. 1B and 2B show a healthy and diseased heart, respectively, left ventricle LV', LV during systole as viewed from the septum (not shown in FIGS. 1B and 2B). In a healthy heart H', the leaflets MVL' of the mitral valve MV' are urged closed by left ventricular pressure. The papillary muscles PM', PM are connected to the heart wall MYO', MYO, near the lower ventricular extremities LE', LE. The papillary muscles PM', PM pull on the leaflets MVL', MVL via connecting chordae tendineae CT', CT. Pull of the leaflets by the papillary muscles functions to prevent valve leakage in the normal heart by holding the valve leaflets in a closed position during systole. In the significantly diseased heart H, the leaflets of the mitral valve may not close sufficiently to prevent regurgitation of blood from the ventricle LV to the atrium during systole.

As shown in FIG. 1B, the geometry of the healthy heart H' is such that the myocardium MYO', papillary muscles PM' and chordae tendineae CT' cooperate to permit the mitral valve MV' to fully close. However, when the myocardium MYO bulges outwardly in the diseased heart H (FIG. 2B), the bulging results in displacement of the papillary muscles PM. This displacement acts to pull the leaflets MVL to a displaced position such that the mitral valve cannot fully close.

Having described the characteristics and problems of congestive heart disease, the treatment method and apparatus of the present invention will now be described.

In general, a jacket of the invention is configured to surround the myocardium MYO. As used herein, "surround" means that jacket provides reduced expansion of the heart wall during diastole by applying constraining surfaces at least at diametrically opposing aspects of the heart. In some preferred embodiments disclosed herein, the diametrically opposed surfaces are interconnected, for example, by a continuous material that can substantially encircle the external surface of the heart.

Figure 3A:
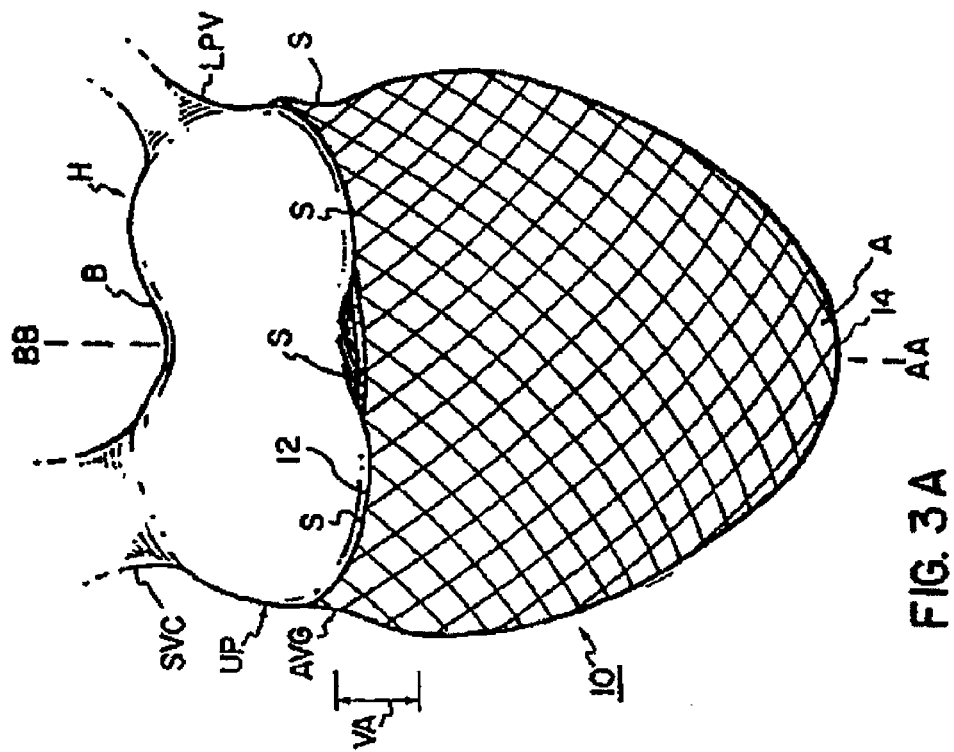
FIG. 3A is a side elevation view of a diseased heart in diastole with the device of FIG. 3 in place.
Figure 3:
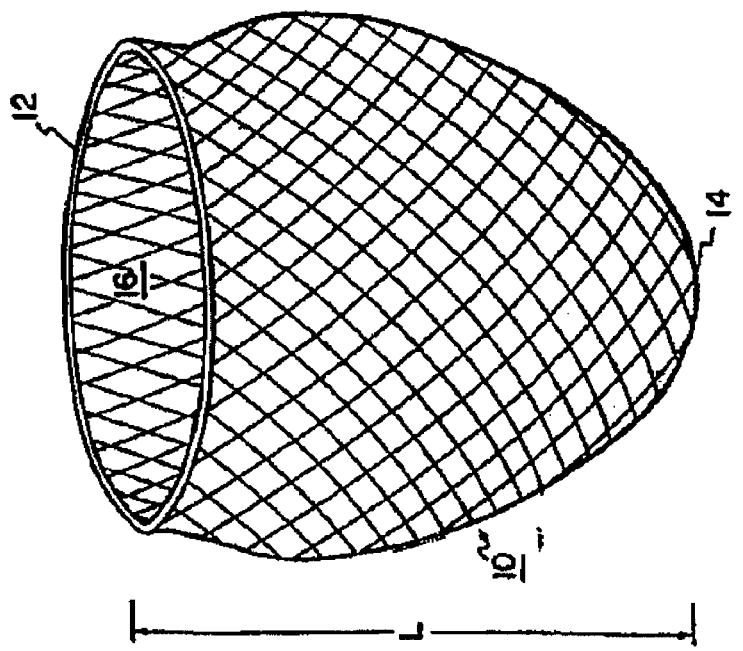
FIG. 3 is a perspective view of a first embodiment of a cardiac constraint device according to the present invention.

With reference now to FIGS. 3, 3A, 4 and 4A, the device of the present invention is shown as a jacket 10 of flexible, biologically compatible material. The jacket 10 is an enclosed knit material having upper and lower ends 12, 14. The jacket 10, 10' defines an internal volume 16, 16' which is completely enclosed but for the open ends 12, 12' and 14, 14'. In the embodiment of FIG. 3, lower end 14 is closed. In the embodiment of FIG. 4, lower end 14' is open. In both embodiments, upper ends 12, 12' are open. Throughout this description, the embodiment of FIG. 3 will be discussed. Elements in common between the embodiments of FIGS. 3 and 4 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be constrained within the volume 16. The jacket 10 can be slipped around the heart H. The jacket 10 has a length L between the upper and lower ends 12, 14 sufficient for the jacket 10 to constrain the lower portion LP. The upper end 12 of the jacket 10 extends at least to the valvular annulus VA and further extends to the lower portion LP to constrain at least the lower ventricular extremities LE.

Since enlargement of the lower portion LP is most troublesome, in a preferred embodiment, the jacket 10 is sized so that the upper end 12 can reside in the A-V groove AVG. Where it is desired to constrain enlargement of the upper portion UP, the jacket 10 may be extended to cover the upper portion UP.

Sizing the jacket 10 for the upper end 12 to terminate at the A-V groove AVG is desirable for a number of reasons. First, the groove AVG is a readily identifiable anatomical feature to assist a surgeon in placing the jacket 10. By placing the upper end 12 in the A-V groove AVG, the surgeon is assured the jacket 10 will provide sufficient constraint at the valvular annulus VA. The A-V groove AVG and the major vessels act as natural stops for placement of the jacket 10 while assuring coverage of the valvular annulus VA. Using such features as natural stops is particularly beneficial in minimally invasive surgeries where a surgeon's vision may be obscured or limited.

When the parietal pericardium is opened, the lower portion LP is free of obstructions for applying the jacket 10 over the apex A. If, however, the parietal pericardium is intact, the diaphragmatic attachment to the parietal pericardium inhibits application of the jacket over the apex A of the heart. In this situation, the jacket can be opened along a line extending from the upper end 12' to the lower end 14' of jacket 10'. The jacket can then be applied around the pericardial surface of the heart and the opposing edges of the opened line secured together after placed on the heart. Systems for securing the opposing edges are disclosed in, for example, U.S. Pat. No. 5,702,343, the entire disclosure of which is incorporated herein by reference. The lower end 14' can then be secured to the diaphragm or associated tissues using, for example, sutures, staples, etc.

In the embodiment of FIGS. 3 and 3A, the lower end 14 is closed and the length L is sized for the apex A of the heart H to be received within the lower end 14 when the upper end 12 is placed at the A-V groove AVG. In the embodiment of FIGS. 4 and 4A, the lower end 14' is open and the length L' is sized for the apex A of the heart H to protrude beyond the lower end 14' when the upper end 12' is placed at the A-V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10'. Such placement is desirable for the jacket 10, 10' to present a constraint against enlargement of the ventricular walls of the heart H.

After the jacket 10 is positioned on the heart H as described above, the jacket 10 is secured to the heart. Preferably, the jacket 10 is secured to the heart H through sutures. The jacket 10 is sutured to the heart H at suture locations S circumferentially spaced along the upper end 12. While a surgeon may elect to add additional suture locations to prevent shifting of the jacket 10 after placement, the number of such locations S is preferably limited so that the jacket 10 does not restrict contraction of the heart H during systole.

Figure 5:
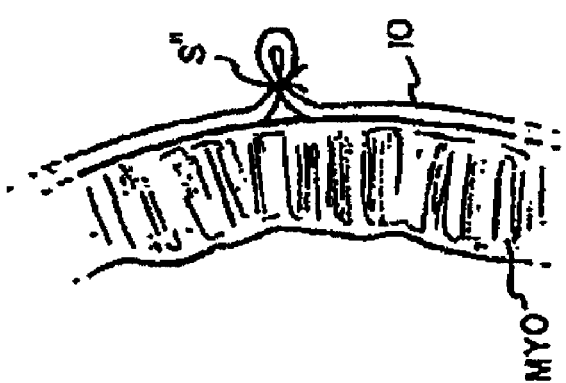
FIG. 5 is a cross-sectional view of a device of the present invention overlying a myocardium and with the material of the device gathered for a snug fit.

To permit the jacket 10 to be easily placed on the heart H, the volume and shape of the jacket 10 are larger than the lower portion LP during diastole. So sized, the jacket 10 may be easily slipped around the heart H. Once placed, the jacket's volume and shape are adjusted for the jacket 10 to snugly conform to the external geometry of the heart H during diastole. Such sizing is easily accomplished due to the knit construction of the jacket 10. For example, excess material of the jacket 10 can be gathered and sutured S" (FIG. 5) to reduce the volume of the jacket 10 and conform the jacket 10 to the shape of the heart H during diastole. Such shape represents a maximum adjusted volume. The jacket 10 constrains enlargement of the heart H beyond the maximum adjusted volume while preventing restricted contraction of the heart H during systole. As an alternative to gathering of FIG. 5, the jacket 10 can be provided with other ways of adjusting volume. For example, as disclosed in U.S. Pat. No. 5,702,343, the jacket can be provided with a slot. The edges of the slot can be drawn together to reduce the volume of the jacket.

The jacket 10 is adjusted to a snug fit on the heart H during diastole. Care is taken to avoid tightening the jacket 10 too much such that cardiac function is impaired. During diastole, the left ventricle LV fills with blood. If the jacket 10 is too tight, the left ventricle LV cannot adequately expand and left ventricular pressure will rise. During the fitting of the jacket 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 2-3 mm Hg) can be tolerated, the jacket 10 is snugly fit on the heart H but not so tight as to cause a significant increase in left ventricular pressure during diastole.

Figure 6:
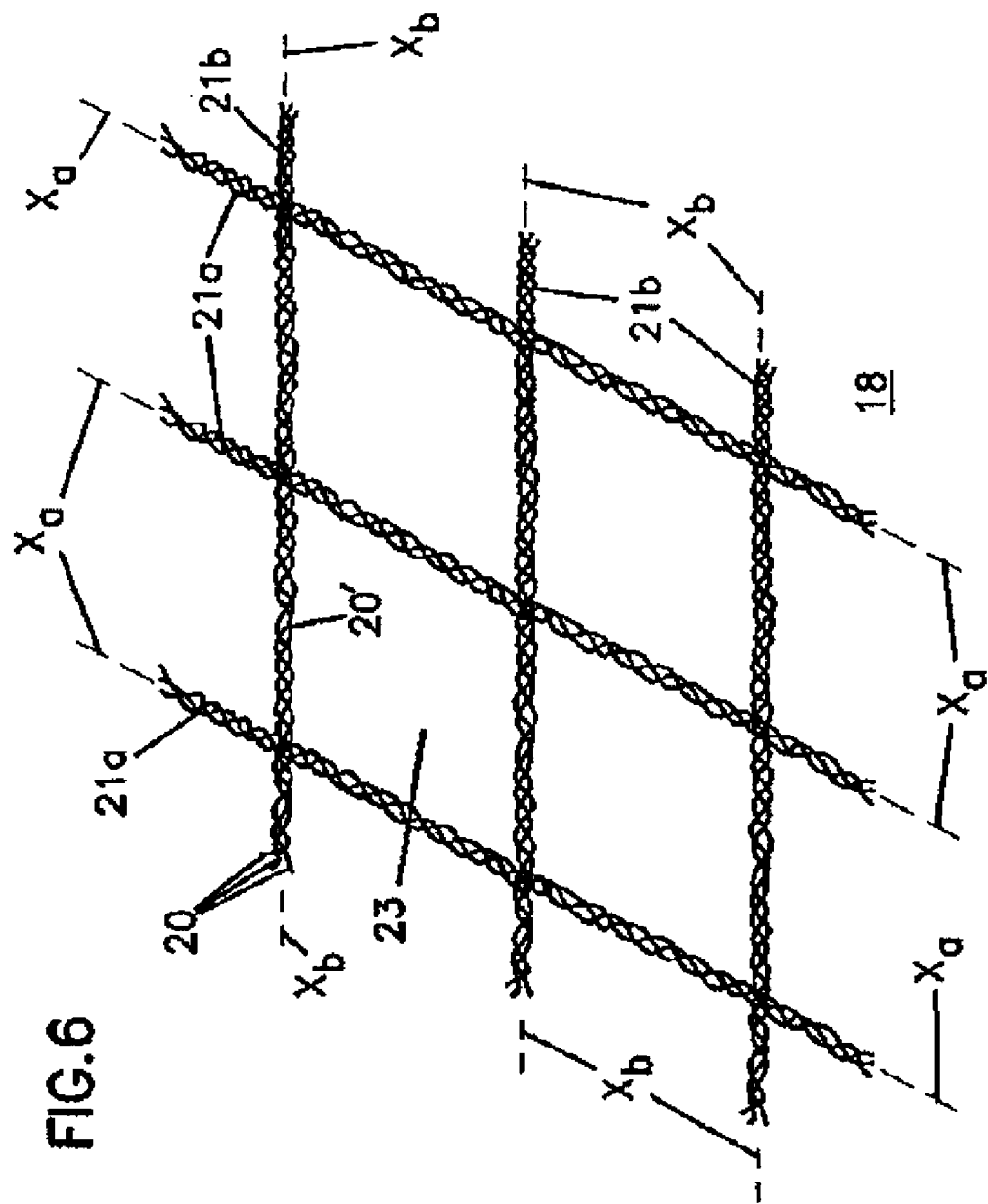
FIG. 6 is an enlarged view of a knit construction of the device of the present invention in a rest state.

As mentioned, the jacket 10 is constructed from a knit, biocompatible material. The knit 18 is illustrated in FIG. 6. Preferably, the knit is a so-called "Atlas knit" well known in the fabric industry. The Atlas knit is described in Paling, Warp Knitting Technology, p. 111, Columbine Press (Publishers) Ltd., Buxton, Great Britain (1970).

The Atlas knit is a knit of fibers 20 having directional expansion properties. More specifically, the knit 18, although formed of generally inelastic fibers 20, permits a construction of a flexible fabric at least slightly expandable beyond a rest state. FIG. 6 illustrates the knit 18 in a rest state. The fibers 20 of the fabric 18 are woven into two sets of fiber strands 21a, 21b having longitudinal axes Xa and Xb. The strands 21a, 21b are interwoven to form the fabric 18 with strands 21a generally parallel and spaced-apart and with strands 21b generally parallel and spaced-apart.

Figure 7:
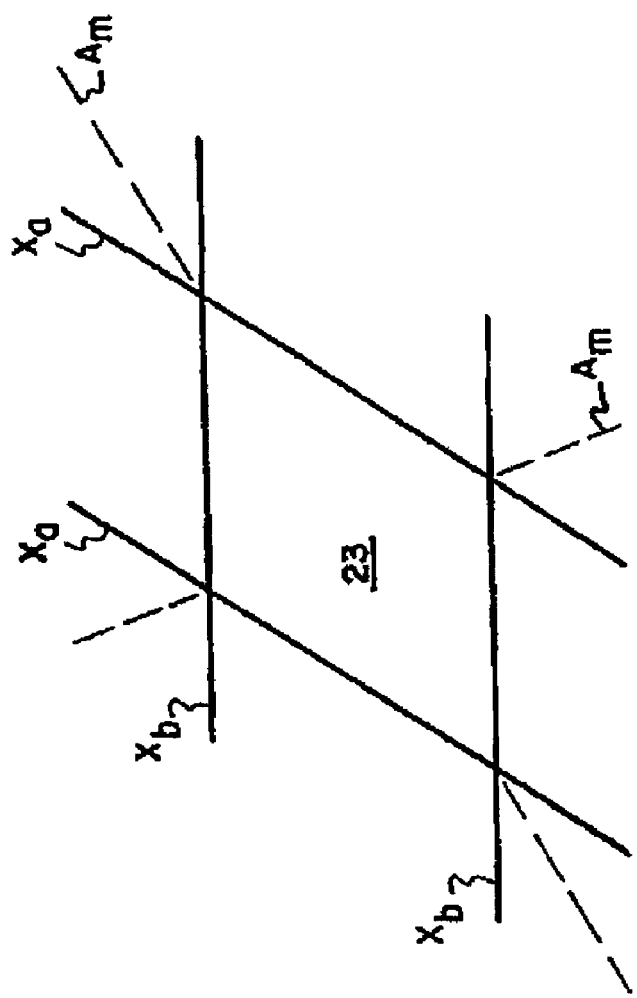
FIG. 7 is a schematic view of the material of FIG. 6.

For ease of illustration, fabric 18 is schematically shown in FIG. 7 with the axis of the strands 21a, 21b only being shown. The strands 21a, 21b are interwoven with the axes Xa and Xb defining a diamond-shaped open cell 23 having diagonal axes Am. In a preferred embodiment, the axes Am are 5 mm in length when the fabric 18 is at rest and not stretched. The fabric 18 can stretch in response to a force. For any given force, the fabric 18 stretches most when the force is applied parallel to the diagonal axes Am. The fabric 18 stretches least when the force is applied parallel to the strand axes Xa and Xb. The jacket 10 is constructed for the material of the knit to be directionally aligned for a diagonal axis Am to be parallel to the heart's longitudinal axis AA-BB While the jacket 10 is expandable due to the above described knit pattern, the fibers 20 of the knit 18 are preferably non-expandable. While all materials expand to at least a small amount, the fibers 20 are preferably formed of a material with a low modulus of elasticity. In response to the low pressures in the heart H during diastole, the fibers 20 are non-elastic. In a preferred embodiment, the fibers are 70 Denier polyester. While polyester is presently preferred, other suitable materials include polytetrafluoroethylene (PTFE), expanded PTFE (ePTFE), polypropylene and stainless steel.

The knit material has numerous advantages. Such a material is flexible to permit unrestricted movement of the heart H (other than the desired constraint on circumferential expansion). The material is open defining a plurality of interstitial spaces for fluid permeability as well as minimizing the amount of surface area of direct contact between the heart H and the material of the jacket 10 (thereby minimizing areas of irritation or abrasion) to minimize fibrosis and scar tissue.

The open areas of the knit construction also allows for electrical connection between the heart and surrounding tissue for passage of electrical current to and from the heart. For example, although the knit material is an electrical insulator, the open knit construction is sufficiently electrically permeable to permit the use of trans-chest defibrillation of the heart. Also, the open, flexible construction permits passage of electrical elements (e.g., pacer leads) through the jacket. Additionally, the open construction permits other procedures, e.g., coronary bypass, to be performed without removal of the jacket.

A large open area for cells 23 is desirable to minimize the amount of surface area of the heart H in contact with the material of the jacket 10 (thereby reducing fibrosis). However, if the cell area 23 is too large, localized aneurysm can form. Also, a strand 21a, 21b can overly a coronary vessel with sufficient force to partially block the vessel. A smaller cell size increases the number of strands thereby decreasing the restricting force per strand. Preferably, a maximum cell area is no greater than about 6.45 $cm^2$ (about 2.54 cm by 2.54 cm) and, more preferably, is about 0.25 $cm^2$ (about 0.5 cm by 0.5 cm). The maximum cell area is the area of a cell 23 after the material of the jacket 10 is fully stretched and adjusted to the maximum adjusted volume on the heart H as previously described.

The fabric 18 is preferably tear and run resistant. In the event of a material defect or inadvertent tear, such a defect or tear is restricted from propagation by reason of the knit construction.

With the foregoing, a device and method have been taught to treat cardiac disease. The jacket 10 constrains further undesirable circumferential enlargement of the heart while not impeding other motion of the heart H. With the benefits of the present teachings, numerous modifications are possible. For example, the jacket 10 need not be directly applied to the epicardium (i.e., outer surface of the myocardium) but could be placed over the parietal pericardium. Further, an anti-fibrosis lining (such as a PTFE coating on the fibers of the knit) could be placed between the heart H and the jacket 10. Alternatively, the fibers 20 can be coated with PTFE.

The jacket 10 is low-cost, easy to place and secure, and is susceptible to use in minimally invasive procedures. The thin, flexible fabric 18 permits the jacket 10 to be collapsed and passed through a small diameter tube in a minimally invasive procedure.

The jacket 10 can be used in early stages of congestive heart disease. For patients facing heart enlargement due to viral infection, the jacket 10 permits constraint of the heart H for a sufficient time to permit the viral infection to pass. In addition to preventing further heart enlargement, the jacket 10 treats valvular disorders by constraining circumferential enlargement of the valvular annulus and deformation of the ventricular walls.

The jacket 10, including the knit construction, freely permits longitudinal and circumferential contraction of the heart H (necessary for heart function). Unlike a solid wrap (such as a muscle wrap in a cardiomyoplasty procedure), the fabric 18 does not impede cardiac contraction. After fitting, the jacket 10 is inelastic to prevent further heart enlargement while permitting unrestricted inward movement of the ventricular walls. The open cell structure permits access to coronary vessels for bypass procedures subsequent to placement of the jacket 10. Also, in cardiomyoplasty, the latissimus dorsi muscle has a variable and large thickness (ranging from about 1 mm to 1 cm). The material of the jacket 10 is uniformly thin (less than 1 mm thick). The thin wall construction is less susceptible to fibrosis and minimizes interference with cardiac contractile function.

Animal test studies on the device show the efficacy of the invention. Test animals were provided with the device 10 of FIG. 3. The animals' hearts were rapidly paced to induce enlargement. After six weeks, animals without the device experienced significant heart enlargement while those with the device experienced no significant enlargement. Further, animals with the device had significantly reduced mitral valve regurgitation.

In addition to the foregoing, the present invention can be used to reduce heart size at the time of placement in addition to preventing further enlargement. For example, the device can be placed on the heart and sized snugly to urge the heart to a reduced size. More preferably, the heart size can be reduced at the time of jacket placement through drugs (e.g., dobutamine, dopamine or epinephrine or any other positive inotropic agents) to reduce the heart size. The jacket of the present invention is then snugly placed on the reduced sized heart and prevents enlargement beyond the reduced size.

From the foregoing, a low cost, reduced risk method and device are taught to treat cardiac disease. The invention is adapted for use with both early and later stage congestive heart disease patients. The invention reduces the enlargement rate of the heart as well as reducing cardiac valve regurgitation.

What is claimed is:

1. A method for treating heart disease in a mammal, including:
   passively constraining expansion of the heart, from an apex of the heart to the heart's A-V groove, along both a first axis aligned generally parallel to a longitudinal axis of the heart and a second axis that is transverse to the first axis; and
   causing the amount of constraint in response to a force applied along the first axis to be different than an amount of constraint in response to a force applied along the second axis.

2. The method of claim 1 wherein causing the amount of constraint in response to a force applied along the first axis to be different than an amount of constraint in response to a force applied to the second axis includes causing the amount of constraint in response to a force applied along the first axis to be less than an amount of constraint in response to a force applied to the second axis.

3. The method of claim 1 wherein passively constraining expansion of the heart includes applying elastic constraint to the heart.

4. A method for treating disease in a mammalian heart having a longitudinal axis and a transverse axis, comprising placing on the mammalian heart a jacket, extending from an apex of the heart to the heart's A-V groove, of flexible and biocompatible material having first and second transverse axes and exhibiting an amount of expansion in response to a force applied to the material along the first axis that is different than an amount of expansion in response to the force applied to the material along the second axis, including placing the jacket with the first axis aligned with the longitudinal axis of the heart and the second axis aligned with the transverse axis of the heart.

5. The method of claim 4 wherein placing the jacket on the heart further includes placing a jacket of flexible and elastic biocompatible material.

6. The method of claim 5 wherein placing the jacket on the heart further includes placing a jacket of material formed from elongated strands.

7. The method of claim 6 wherein placing the jacket on the heart further includes placing a jacket of material having open cells.

8. The method of claim 7 wherein placing the jacket on the heart further includes placing a jacket of material formed from metal elongated strands.

9. The method of claim 8 wherein placing the jacket on the heart includes applying a jacket of enclosed material having an open upper end over an apex of the heart.

10. The method of claim 7 wherein placing the jacket on the heart includes placing a jacket exhibiting an amount of expansion in response to the force applied to the material along the first axis that is greater than the amount of expansion in response to the force applied to the material along the second axis.

11. The method of claim 10 wherein placing the jacket on the heart further includes placing a jacket of material formed from polymer elongated strands.

12. The method of claim 4 wherein placing the jacket includes placing a jacket exhibiting an amount of expansion in response to the force applied to the material along the first axis that is greater than the amount of expansion in response to the force applied to the material along the second axis.

13. The method of claim 4 wherein placing the jacket on the heart includes applying a jacket of enclosed material having an open upper end over an apex of the heart.

14. A method, including causing a jacket of flexible and biocompatible material having first and second transverse axes and exhibiting an amount of expansion in response to a force applied to the material along the first axis that is different than an amount of expansion in response to the force applied to the material along the second axis to be placed on a mammalian heart, extending from an apex of the heart to the heart's A-V groove, having a longitudinal axis and a transverse axis for purposes of treating disease of the heart, including providing the jacket configured for placement with the first axis aligned with the longitudinal axis of the heart and the second axis aligned with the transverse axis of the heart.

* * * * *